United States Patent [19]
Mainzer et al.

[11] Patent Number: 5,827,552
[45] Date of Patent: Oct. 27, 1998

[54] PRODUCTION OF FERMENTED FOOD PRODUCTS

[75] Inventors: Stanley E. Mainzer, Burlingame; Sienna Yoast, La Honda; Robin M. Adams; Tony V. Palombella, both of San Francisco; Brian F. Schmidt, Half Moon Bay, all of Calif.

[73] Assignee: Gist-Brocades B.V., Netherlands

[21] Appl. No.: 333,934

[22] Filed: Nov. 3, 1994

Related U.S. Application Data

[63] Continuation of Ser. No. 48,399, Apr. 14, 1993, abandoned, which is a continuation of Ser. No. 912,020, Jul. 9, 1992, abandoned, which is a continuation of Ser. No. 826,698, Jan. 28, 1992, abandoned, which is a division of Ser. No. 274,584, Nov. 22, 1988, abandoned.

[51] Int. Cl.$^6$ .............................. A23C 9/12; A23C 9/13; C12N 1/21; C12N 15/09; C12P 1/04
[52] U.S. Cl. .................................. 426/7; 426/34; 426/42; 426/43; 426/61; 435/99; 435/170; 435/172.1; 435/172.3; 435/207; 435/252.9; 435/252.3; 435/252.4
[58] Field of Search .................................. 426/34, 42, 43, 426/61, 7; 435/34, 99, 207, 252.3, 525.9, 170, 172.3, 252.4, 172.1

[56] References Cited

U.S. PATENT DOCUMENTS

| | | | |
|---|---|---|---|
| 4,734,361 | 3/1988 | Murao et al. | 435/34 |
| 4,861,718 | 8/1989 | Hirata et al. | 435/207 |
| 4,977,088 | 12/1990 | von Wright et al. | 435/252.3 |

OTHER PUBLICATIONS

Premi et al (1972) "Lactose–hydrolyzing enzymes of *Lacto bacillus* species" Applied microbiology 24:51–57.
Estell (1993) "Engineering enzymes for improved performance in industrial applications" J. Biotechnol. 28:52–30.
Westerhoff (1995) "Subtlety in control—metabolic pathway engineering " Trends Biotech. 13: 242–244.
Miller (1972) Experiments in Molecular Genetics, Cold Spring Harbor Lab.
Colb et al. (1977) PNAS vol. 74(12): 3637–3641.
Schmidt et al. (1989) J. Bacternol. vol. 171(2): 625–635.
Sakar et al. (1986) Biochemistry vol. 25:2778–2781.
Ahmad, et al., "Cloning of the lux genes into *Lactobacilluscasei* and *Streptococcus lactis*: phosphate–dependent light production" Biochem. Soc. Transactions, p. 1068 (1988).
Batt, "Genetic Engineering of Lactobacillus"*Food Tech* pp. 95–112 (Oct 1986).
Biozet, et al., "Transfection of *Lactobacillus bulgaricus* Protoplasts by Bacteriophage DNA" *Applied and Enviromental Microbiology* 54(12):3014–3018 (Dec. 1988).
Chassy, et al. "Transformation of *Lactobacillus casei* by electroporation" *FEMS Microbiol. Letters* 44:173–177 (1987).
Chassy, "Prospects for the Genetic Manipulation of Lactobacilli" *FEMS Microbiol. Rev.* 46:297–312 (1987).

Bacterial Starter Cultures for Foods, Eds. Stanley E. Gilliland, CRC Press, Inc. Boca Raton, FL pp. 44–47.
Estell, et al., "Engineering an enzyme by Site–directed Mutagenesis to Be Resistant to Chemical Oxidation" *J. of Biol. Chem.* 260(11)6518–6521 (Jun. 1985).
Henner, et al., "Localization of *Bacillus subtilis* sacU(Hy) Mutations to Two Linked Genes with Similarities to the Conserved Procaryotic Family of Two–Component Signaling Systems" *J. of Bacteriology* 170(11):5102–5109 (Nov. 1988).
Kasumi, et al., "Purification and Enzymatic Properties of Glucose Isomerse from *Streptomyces griseofuscus*, S–41" *Agric. Biol. Chem.* 45(3):619–627 (1981).
Langella, et al., Conjugal transfer of plasmid pIP501 from *lactococcus lactis* to *Lactobacilus delbruckii* subsp. *bulgaricus* and *Lactobacillus helveticus FEMS Microbiol. Letters* 60:149–152 (1989).
Lin, et al., "Genetic Transformation of Rifampicin Resistance in *Lactobacillus acidophilus*" *J. of General Microbiology* 132:2107–2111 (1986).
Marston, F., "The purification of eukaryotic polypeptides synthesized in *Escherichia coli*" *Biochem. J.* 240:1–12 (1986).
McKay, et al., Lactose Utilization by Lactic Acid Bacteria: A Review *Dairy Sci. Abstr.* 33(7):493–499 (1971).
Morelli, et al., "Lactobacillus Protoplase Transformation" *Plasmid* 17:73–75 (1987).
Poolman, et al., "Lactose Transport System of *Streptococcus thermophilus:* a Hybrid Protein with Homology to the Melibiose Carrier and Enzyme III of Phosphoenolpyruvate–Dependent Phosphostransferase Systems" *J. Bacteriology* 171(1): 244–253 (Jan.1989).
Scheirlinck, et al., "Integration and Expression of α–Amylase and Endoglucanase Genes in the *Lactobacillus plantarum* Chromosome" *Applied Envir. Microbiol.* 55(9):2130–2137 (Sep. 1989).
Stahl, et al., "Replacement of the *Bacillus subtilis* Subtilisin Structural Gene with an In Vitro–Derived Deletion Mutation" *J. Bacteriology* 158(2):411–418 (May 1984).
Van, et al., "Manipulation of the morphogenetic pathways of tobacco explants by oligosaccharins" *Nature* 314:615–617 (Apr. 1985).
Vieira, et al., "Production of Single–Stranded Plasmid DNA" *Methods in Enzymology* 153:3–11(1987).

*Primary Examiner*—Jasemine C. Chambers
*Assistant Examiner*—Scott D. Priebe
*Attorney, Agent, or Firm*—Morrison & Foerster, LLP

[57] ABSTRACT

This invention discloses novel methods of making fermented food products such as yogurt. It also discloses novel *Lactobacillus bulgaricus* organisms for making fermented food products which are conditionally sensitive, that is, operate to metabolize a desired compound normally under the processing conditions for fermented food products but slow or decrease in activity beyond what is normal under the routine storage temperatures for the fermented food products. Such fermented food products exhibits improved shelf life and long-term taste.

6 Claims, No Drawings

PRODUCTION OF FERMENTED FOOD PRODUCTS

CROSS-REFERENCED RELATED APPLICATIONS

This application is a Continuation of application Ser. No. 08/048,399 filed Apr. 14, 1993, now abandoned, which is a Continuation of application Ser. No. 07/912,020 filed Jul. 9, 1992, now abandoned, which is a Continuation of application Ser. No. 07/826,698 filed Jan. 28, 1992, now abandoned, which is a Division of application Ser. No. 07/274,584 filed Nov. 22, 1988, now abandoned.

BACKGROUND OF THE INVENTION

1. Field of the Invention

The present invention relates to novel methods of making a fermented food product, especially fermented dairy products. Further, the invention relates to novel mutant strains of Lactobacillus bulgaricus (L. bulgaricus) and methods of making them which are useful in the preparation of yogurt and other fermented food products. The invention also relates to novel mutant genes and organisms transformed with such genes.

2. Background Art

A variety of food products are available worldwide which depend on active bacterial cultures in the final form of the food product for flavor, preservation of quality, claimed health benefits and/or pH. Examples are fermented vegetable products, such as sauerkraut from cabbage and pickles from cucumbers; fermented fish products such as fish paste or burongdalog; fermented seeds such as coffee or cocoa beans; fermented starch-rich food products; fermented meat products; fermented cassava; or fermented fruit juices. Particularly important are fermented dairy products such as yogurt, sour cream, crème fraché; buttermilk, and the like. These fermented dairy products depend, to a certain degree, on organisms which metabolize lactose to produce flavor and lower the pH to preserve the food. These products can be especially important to those people with lactose intolerance; i.e., the inability or difficulty in metabolizing lactose.

Yogurt is an extremely popular fermented dairy product. Microbiologically, yogurt may be defined in the United States and many other countries as the end-product of a controlled fermentation of milk with a mixture of Streptococcus thermophilus (S. thermophilus) and L. bulgaricus. The fermentation is carried out within a temperature range of 35°–45° C. with about 42°–45° C. being preferred. Early in the incubation, S. thermophilus grows rapidly dominating the fermentation and lowering the oxidation-reduction potential of the system. L. bulgaricus grows slowly during the early fermentation but liberates sufficient amounts of peptides and amino acids to stimulate growth of S. thermophilus which results in moderate production of lactic acid, acetic acid, acetaldehyde, diacetyl and formic acid. When the pH of the fermentation mix is sufficiently lowered to around 5.5, the rapid growth of S. thermophilus is arrested and the growth of L. bulgaricus is favored. Depletion of oxygen from the system and the availability of formate is believed to stimulate such growth. The major portion of lactic acid and acetaldehyde necessary for the characteristic flavor of yogurt is contributed by the L. bulgaricus which has been aided by the initial activity of the S. thermophilus component. When the pH drops further to about 5.0 or less the product is cooled to about 10° C. or less for storage. Although the rate of production of lactic acid is diminished under the normal storage conditions of yogurt (4°–10° C.), production of lactic acid continues to such a degree that the yogurt product is, depending on strain or process, rendered unpalatable (sour) after 3 or 4 weeks. Attempts to further slow or arrest the production of lactic acid during storage while maintaining viable organisms have been largely unsuccessful. Preservatives have been tried but have the undesirable side effect of affecting the viability or killing the yogurt organism. Attempts at mutating the organism directly; e.g., through chemical or other mutagenesis techniques have not only produced organisms with decreased lactic acid production at lower temperature and pH, but organisms also showing a proportional decrease in lactic acid production at fermentation temperatures and a decreased growth, thus producing an unsatisfactory yogurt product or products which are limited to the strain which has been mutated (with an unknown effect), which can not be easily transferred to new starters (see U.S. Pat. No. 4,734,361 to Meiji Milk Products wherein a method is described for isolating a naturally-occurring variant of Lactobacillus bulgaricus). This temperature-sensitive organism produces less than 0.1% lactic acid at 10° C. for 7 days. This method is dependent on a strain being present which matches the description of the invention, and, to date, only one such natural isolate is known to exist, OLL 1074. Currently no cultures, especially of L. bulgaricus, are available which combine the desired needs of texture and taste while maintaining the extended lowered metabolism under storage temperature, have the site of mutation defined and are transferable to new starters.

It would be useful to construct a L. bulgaricus which exhibited both decreased production of lactic acid at the storage temperature of yogurt yet still retained acceptable levels of activity under production conditions of yogurt where the mutation is defined and which could be transferable to new starters starting from any single strain of L. bulgaricus and remains viable in the yogurt product. It would also be useful to have such organism produce less acid at temperatures below about 20° C. or at about pH 5.5 or lower in order to give more flexibility during production and handling after production. Furthermore, it would aid in the manufacture of fermented products to have the fermentation slow or stop after reaching a certain range of temperature and/or pH rather than using a quick refrigeration to decrease the rate of acid formation.

SUMMARY OF THE INVENTION

It is an object of this invention to provide novel organisms and methods for obtaining them where such organisms are for use in fermented food products where the organism exhibits decreased metabolism beyond what is normal under storage temperatures of the fermented food products, yet retains its activity and viability under production conditions of the fermented food product.

It is further an object of the invention to provide novel fermented food products containing viable organisms which, under normal storage conditions of the fermented food products, develop excess acidity or off flavors more slowly than previously fermented food products containing viable organisms.

It is also an object of the invention to provide methods of producing fermented food products.

It is also an object of this invention to provide novel organisms which exhibit decreased production of lactic acid at the storage conditions of yogurt or other food products, yet essentially the novel organisms retain their activity and viability under production and storage conditions. It is a further object of this invention to provide a method of obtaining such organisms.

Even further it is an object of the invention to provide a method of producing yogurt or other food products which simplifies both the processing and handling of the product. It is yet a further object of this invention to provide a yogurt or other food products containing viable organisms which are storage stable below about 20° C. and/or at about pH 5.5. Accordingly, the invention comprises a method for making a fermented food product comprising:

a) selecting an organism suitable for making a fermented food product, the organism being a mutant organism not found in nature which produces a non-naturally occurring variant enzyme which metabolizes a substrate to a desired product in a fermented food product under normal fermentation conditions but under storage conditions of the fermented food product the variant enzyme metabolizes the substrate at a rate of at least about 20% less than the enzyme produced by the organism found in nature from which the variant enzyme is derived, yet retains at least about 90% of the necessary rate of such metabolism when compared with said enzyme produced by the organism found in nature under the production conditions of the fermented food product;

b) adding the organism selected in step a) to an unfermented food product containing a substrate capable of being metabolized by the variant enzyme to the desired product; and c) fermenting the mixture of step b) under conditions favorable for the production of the fermented food product.

Also, the invention relates to a novel organism comprising a mutant organism not found in nature, suitable for the production of a fermented food product, which organism produces a non-naturally occurring variant enzyme which metabolizes a substrate to a desired product in the fermented food under the storage conditions of the fermented food product at a rate of at least about 20% less than the enzyme produced by the organism found in nature from which the variant enzyme is derived, yet retains at least about 90% of the rate of metabolism needed for production of the fermented food product when compared with the enzyme produced by the organism found in nature, under the production conditions of the fermented product.

Further the invention also relates to a method of making yogurt which comprises:

a) selecting S. thermophilus and L. bulgaricus organisms suitable for making yogurt, the L. bulgaricus organisms being a mutant L. bulgaricus not found in nature which organism produces a non-naturally occurring variant enzyme which metabolizes lactose to lactic acid under the storage conditions of yogurt at a rate of at least about 20% less than the enzyme produced by the L. bulgaricus found in nature it is derived from yet retains at least about 90% of the rate of such metabolism under the production conditions of yogurt;

b) adding the organisms of step a) to milk;

c) fermenting the mixture of step b) under conditions favorable for the production of yogurt; and d) bringing the temperature of the fermented mixture of c) to the desired storage temperature.

And even further, the invention relates to a method of mutating an organism for use in making a fermented food product which comprises:

a) selecting an organism suitable for use in making a fermented food product;

b) removing the gene which codes for an enzyme involved in the metabolism of a substrate to a desired product from the organism of step a);

c) inserting the gene of b) in a replicable plasmid;

d) performing mutations on a plurality of the plasmids of step c);

e) selecting those mutations of step d) which, when used to transform an organism and produce a variant enzyme, said enzyme exhibits decreased activity at a rate of at least about 20% less than the enzyme produced by the organism found in nature from which the variant enzyme is derived under the storage conditions of the fermented food product but where said variant enzyme retains at least about 90% of its activity at the production conditions of the fermented food products when compared with the enzyme produced by the organism found in nature from which the mutant enzyme is derived; and f) inserting and expressing the selected mutated gene of step e) into an organism suitable for the production of the fermented food product.

This is done preferably after deleting the corresponding native enzyme.

The invention also relates to a novel fermented food product comprising a viable mutant organism not found in nature which organism produces a non-naturally occurring variant enzyme which metabolizes a substrate to a desired product under the normal storage conditions of the fermented food product at a rate of at least about 20% less than the enzyme produced by the organism found in nature from which the variant enzyme is derived, yet wherein said variant enzyme retains at least about 90% of the rate of metabolism when compared with said enzyme produced by the organism found in nature under the production conditions of the fermented food product.

The invention also relates to a viable mutant *L. bulgaricus*, not obtainable by generalized mutation, isolatable from existing cultures, or found in nature, suitable for the production of yogurt or other dairy products which produces an enzyme which metabolizes lactose to lactic acid under the storage condition of yogurt (preferably a temperature below about 20° C., more preferably 4°–10° C. or at a pH of about 5.5 or less) at a rate of at least about 20% less than the enzyme produced by the *L. bulgaricus* found in nature which it is derived from, yet retains at least about 90% of the rate of such metabolism under the production conditions of yogurt.

DETAILED DESCRIPTION OF THE INVENTION

Fermented food products are those foods in which an active bacterial culture remains in a food and wherein the active bacterial culture has metabolized a specific substrate to produce a desired taste, pH or lowered pH to preserve the food. As discussed above, such foods and the organisms to produce them, are widely known, for example: vegetable products may use Pseudomonas, Flavobacterium, Aerobacter, Bacillus, Leuconostoc, and Lactobacillus; fermented fish products may use *Leuconostoc mesenteroides, Lactobacillus brevis, Pediococcus cerevisea, Lactobacillus plantarium,* and Bacillus species; fermented seed may use *Bacillus natto;* fermented starch-rich materials may use Corynebacterium species; fermented meat products may use Lactobacillus species; fermented melons may use Corynebacterium species, *Geotrichum candidum,* Leuconostoc species; fermented fruit juices may use Zymononas species; soy sauce uses Aspergillus species; and wine and beer use Saccharomyces species. As other species of bacteria, yeast and fungi are developed for food, it is clear that they would be covered also and are contemplated within the scope of the invention. A preferred fermented food product is the fermented dairy products, especially yogurt.

The desired substrate as used herein is the substrate the selected organism will metabolize in the metabolic pathway of the final compound which produces a desired taste or pH. So, for example, when using a *L. bulgaricus* organism to produce yogurt, the desired substrate is lactose or an intermediate which is metabolized to lactic acid.

As used herein the normal storage conditions refers to the physical conditions such as pH or temperature at which one would hold the food while awaiting consumption.

Previous attempts to affect the storage performance of food grade organisms, such as *L. bulgaricus*, for making fermented food products without affecting the fermented food-making capabilities have been largely unsuccessful. Through classical mutation techniques, e.g., chemical, u.v., etc., attempts have been made to alter, i.e., organisms such as *L. bulgaricus* in the metabolic pathway have been global; i.e., a decrease in the metabolic rate at storage conditions was accompanied by an unacceptable change in metabolic rate at production conditions or, most importantly, they have been undefined or nontransferable to other starter strains of *L. bulgaricus*. It has been discovered unexpectedly that when a gene coding for an enzyme in the metabolic pathway is mutated in vitro , i.e., the gene removed from the organism, that chemical mutation of the gene will produce a percentage of variants which exhibit at least about a 20% decrease in metabolism below about 20° C. and/or about pH 5.5 or less, yet retain at least about 90% activity at the production conditions of the fermented food products when expressed in a transformed organism. In a preferred environment the mutants selected have essentially no change in activity of the modified enzyme. The measurement of change is against the original form of the enzyme found in nature. It is, of course, possible to achieve such mutations after several successive generations of gene mutations so that a direct comparison of metabolic rates of successive mutants does not appear to produce the desired change. The change in the desired mutant would still, however, be compared against the form of the organism found in nature. The mutated gene may then be used to transform another similar organism (or other desired organism) to achieve the organism of the invention using methods known in the art.

As used herein *L. bulgaricus* organisms suitable for making yogurt or other fermented dairy products are widely utilized naturally-occurring food grade organisms useful in various commercial applications. As described above, *L. bulgaricus* is used as one of the organisms in the production of yogurt or other fermented dairy products. *L. bulgaricus* produces a number of enzymes which are responsible for the metabolism of lactose to lactic acid. Most notable is a permease which is responsible for the transport of lactose into the *L. bulgaricus* organism and β-galactosidase which metabolizes lactose directly to glucose and galactose. Glucose is further metabolized and other enzymes in this pathway include glucokinase, phosphoglucose isomerase, phosphofructokinase, aldolase, triose phosphate isomerase, phosphoglycerate kinase, phosphoglyceromutase, enolase, pyruvate kinase, and lactate dehydrogenase (Henry R. Mahler and Eugene Cordes, In Biological Chemistry, Harper & Row, New York, New York, 1966). In other organisms, other pathways such as the pentose phosphate or Entner-Doudoroff pathway, among others could be used (Gerhard Gottschalk, "In Bacterial Metabolism", 1979). Permease and β-galactosidase are especially interesting because in the lactose to lactic acid pathway they are the only enzymes in this metabolic pathway which do not appear to be substantially involved in some other metabolic function.

Preferred genes in the lactic acid pathway for mutation are those coding for lactose permease. See. The Lactose Transport System of *Streptococcus thermophilus*: "A Hybrid Protein with Homology to the Melibiose Carrier and Enzyme III of PEP-Dependant Phosphotransferase Systems" from Genencor attached, B. Poolman, T. Royer, S. Mainzer and B. Schmidt, J. of Bacteriol. (in press) incorporated by reference, *Molec. Gen. Genet.*, pp. 159, 239–248 (1978); *Nature*, Vol. 283, pp. 541–545, Feb. 7, 1980; and β-galactosidase (see *The Cloning, Expression and Sequencing of the Beta-Galactosidase Gene from Lactobacillus Bulgaricus into E. Coli*, from Genencor presented at the Second Symposium on Lactic Acid Bacteria on Sep. 22–25, 1987, Wageningen, The Netherlands by Schmidt, B. et al. J. of Bacteriol. (in press) incorporated herein by reference). As used in the specification and claims, vector relates to a gene sequence which includes at least the gene coding for the enzyme of interest. This form could be linear DNA, a plasmid of some type, or the like. The vector may be of the replicable type, a type which is incorporated into the chromosome for replication or a gene sequence which must be combined with some other gene sequence or shuttle mechanism for incorporation into an organism in a replicable form.

When producing the mutant organism of the invention, the vector may be mutated in vitro by any number of chemical mutagens. For instance, the single and double stranded chemical mutagenesis procedures illustrated in the examples. Other methods of mutation include alpha thiol misincorporation, cassette mutagenesis or other methods of site specific mutagenesis. Applicant has noted that approximately 1 in 1000–5000 transformants appear to achieve the desired attributes of the invention. The results are reproducible and just a matter of screening a number of mutants. In order to test such a large number of variants in a reasonable time period, the mutated gene can be reinserted in a replicable and expressible form, either in a plasmid or integrated into the chromosome of an organism and tested. One satisfactory preferred method (see also examples) involves construction of a plasmid using the β-galactosidase gene, performing the mutagenesis in vitro on the plasmid and then transforming a relatively easily replicable organism like *E. coli* (or *L. bulgaricus* or *L. casei*). The transformed organisms can be screened to see if reaction conditions are such that they meet the desired conditions. Where the clone normally produces a similar enzyme to that being expressed, it is desirable that that gene for the similar enzyme be removed from the host. In this example, the naturally occurring β-galactosidase gene could be removed from the host *L. bulgaricus*.

Primarily, there will be two types of preferred mutants screened for: temperature sensitive conditional ($C^s$) and pH sensitive conditional ($PH^s$), although other parameters are possible. Some combination of types of mutants may obviously also be desirable. For example, a temperature conditional mutant for use in the production of yogurt will be one which exhibits a decrease in metabolism of lactose below about 20° C., yet only exhibit a 10% or less decrease in activity at processing temperatures; i.e., 35° C.–45° C. Likewise, a pH conditional mutant for use in the production of yogurt will exhibit a decrease in activity of at least about 20% at pH's of about 5.5 or less and retain at least about 90% activity at the beginning processing pH of the fermented food product compared to wild-type enzymes.

Once the proper gene sequence is selected from the variant enzymes, it can be reincorporated into the organism of choice in such a manner that it replicates; i.e., plasmid or homologous genome integration, preferably, as suggested above, with the corresponding native gene sequence previously removed. The transformed organism of the invention can then be used to produce a fermented food product with improved shelf life using conventional techniques (without introducing any foreign DNA since only the mutated enzyme will be replaced in the organism). In a preferred embodiment the fermented food product made will have a longer shelf life, better taste and texture than the fermented food product made without this invention after extended storage.

The following examples are representative of the invention and not intended to be limiting. One skilled in the art will see that the success rate is such that the experiments are easily reproduced and as such, no deposits have been made of organisms or genes. One skilled in the art could devise other screens or use other direct mutagenesis techniques without undue experimentation.

DESCRIPTION OF THE PREFERRED EMBODIMENTS

Chemical Mutagenesis of β-Galactosidase Gene
1. Double-Stranded Method
   Plasmid Construction.

Two BamHI fragments were deleted from the pKK223-3 vector (Pharmacia Molecular Biologicals, Piscataway, N.J. 08854) that carries the *L. bulgaricus* β-galactosidase gene on the 7 kb insert. The resulting plasmid has the tac promoter (de Boer, H. A. et al. *PNAS* Vol. No. 78, pg. 21 (1983)) removed from the pKK223-3 vector and the β-galactosidase gene is now on a 4.3 kb HindIII-BamHI fragment.

Mutagenesis.

Plasmid DNA (~5 ug) in 10 mM Tris-HCl and 1 mM $Na_2EDTA$ (pH 7.6) was added to 7 ul of 1M potassium phhosphate (pH 5.2), 20 ul 3M sodium acetate (pH 4.5) and water for a final volume of 0.1 ml. Then 0.1 ml of 2M hydroxylamine (HA) in ethylene glycol was added to the DNA solution. The reaction was incubated at 65° or 75° C. with 20 ul aliquots removed at various times from 0 to 10 minutes. The DNA in the aliquots was immediately precipitated with 2 ul 3M sodium acetate and 50 ul ethanol. The dried precipitate was dissolved in 30 ul 10 mM Tris-HCl and 1 mM $Na_2EDTA$ (pH 7.6) and used to transform *E. coli* JM105, JM108 and JM109 cells (Maniatis, T.; Fritsch, E. F.; Sambrook, J., "Transformation Protocol", *In Molecular Cloning: A Laboratory Manual*, p. 250, 1983). The transformation mix was plated on Luria Agar plates containing X-gal (5-Bromo-4-chloro-3 indoyl-B-D glactopyrandside, Sigma Chemical Co., St. Louis, Mo.) and 50 ug/ml carbenicillin. Mutants were screened as discussed below.

2. Single-Stranded Method
   Plasmid Construction.

The β-galactosidase gene on the 4.3 kb HindIII-BamHI fragment was cloned into pUC118. Single-stranded DNA was isolated from this clone after the addition of M13 helper phage (the pUC118 vector has a 470 bp M13 replicon inserted into the NdeI site of pUC18). Unique PstI and XbaI sites were introduced at nucleotides 23 and 441, respectively, using oligonucleotide site directed mutagenesis. Single-stranded DNA from this mutant was used in the chemical mutagenesis described below.

Mutagenesis.

First, ethylene glycol, 50 ul, was added to 150 ul of 1M sodium acetate containing 1M methoxylamine hydrochloride (MA) (pH 5). Then single-stranded DNA in 10 ul (~5 ug) was added and incubated in the dark at 50° C. for 45, 60, 90 or 120 minutes. The reaction was stopped by ethanol precipitation and JM105 cells transformed and plated as described above. The transformation mix was plated on X-gal-containing medium and screened as described below.

Selection of Temperature Conditional Mutants

A nitrocellulose filter is placed on a Luria Agar carbenicillin plate. The transformed *E. coli* are spread on top and colonies grown overnight at 37° C. Two nitrocellulose replica filters are made from this master. One filter is layered on an X-gal plate at 37° C. and β-galactosidase activity is detected by the appearance of blue colonies. The other filter is layered on a Luria Agar carbenicillin plate, grown for about 20 hours at 37° C. then placed at 4° C. overnight. The filter is lifted off the plate and placed on an X-gal plated at 4° C. overnight. Colonies of the invention are those that are blue at 37° C. but are white at 4° C.

Second Round Mutagenesis.

Starting with the $C^s4$ variant phenotype which is blue on 37° C. X-gal plates and using MA as a mutagen, additional mutants were generated through a second round of mutagenesis.

Mutagenesis Results

Approximately 12,000 colonies have been screened using the double- and single-stranded mutagenesis methods. In a typical experiment, 0.1–0.2% of the total colonies are white at 37° C. and 2–4% are white at 4° C. Colonies that were blue at 37° C. and white at 4° C. were double checked for the temperature conditional phenotype by replating at the high and low temperatures. Plasmid DNA was isolated from these colonies and used to transform JM105 or JM109 *E. coli* cells and a consistent temperature conditional β-galactosidase activity was conferred by the plasmids. To localize the region of the mutation, various restriction fragments of the mutant gene were exchanged for wild-type fragments. A characterization of 3 of the mutants is given below:

CS1 and CS4: Wild-type plasmids and plasmids isolated from this mutant were digested with NcoI and then the 1282 bp NcoI fragments and the vector fragments (carrying the rest of the β-galactosidase gene) were isolated from polyacylamide gels. The mutant 1282 bp fragment was ligated into the wild-type vector and the 1282 bp wild-type fragment was ligated into the mutant vector. The construction with the 1282 bp NCOI mutant restriction fragment was temperature conditional while the other construction gave a wild-type phenotype. Thus, the temperature conditional mutation lies between nucleotides 792 and 2074 (the NcoI fragment) in the structural gene of *L. bulgaricus* β-galactosidase in this mutant.

CS2: The structural gene for β-galactosidase from wild-type and mutant plasmids were removed on a BamHI-XbaI fragment. The wild-type structural gene was hooked up to the mutant promoter and the mutant structural gene was hooked up to the wild-type promoter. Only the construction containing the mutant structural gene had a temperature conditional phenotype. Thus, the mutation is in the structural part of the gene and not in the promoter region in this mutant.

CS3: By using identical methods as described for CS2, the mutation in this mutant was also localized in the structural gene and not in the promoter region.

The following table lists the results of the 27 β-galactosidase mutants obtained in the screen:

PHENOTYPES OF β-GALACTOSIDASE MUTANTS

| Mutant | Plasmid | Mutagen | *Colony color after 24 hours | |
|---|---|---|---|---|
| | | | 37° C. | 4° C. |
| Control (wt) | PKK223-3 or PUC118 | — | Blue | Blue |
| $C^s$ 1 | PKK223-3 | HA | Light blue | White |
| $C^s$ 2 | PUC118 | MA | Blue | White |
| $C^s$ 3 | PUC118 | MA | Blue | White |
| $C^s$ 4 | PUC118 | MA | Blue | Light Blue |
| $C^s$ 5 | PUC118 | MA | Blue | White |
| $C^s$ 6 | PKK223-3 | HA | Blue | Light Blue |
| $C^s$ 7 | PKK223-3 | HA | Light Blue | Light Green |
| $C^s$ 8 | PKK223-3 | HA | Light Blue | Light Green |
| $C^s$ 11 | PKK223-3 | HA | Light Blue | Light Green |
| $C^s$ 12 | PKK223-3 | HA | Blue | Light Blue |
| $C^s$ 13 | PKK223-3 | HA | Light Blue | Light Blue |
| $C^s$ 14 | PKK223-3 | HA | Light Blue | Light Blue |
| $C^s$ 15 | PKK223-3 | HA | Blue | Light Blue |
| $C^s$ 16 | PKK223-3 | HA | Blue | White |
| $C^s$ 18 | PKK223-3 | HA | Light Blue | White |
| $C^s$ 19 | PKK223-3 | HA | Light Blue | White |
| $C^s$ 20 | PKK223-3 | HA | Blue | Light Green |
| $C^s$ 21 | PKK223-3 | HA | Blue | Light Green |
| $C^s$ 22 | PKK223-3 | HA | Light Blue | Light Blue |
| $C^s$ 23 | PKK223-3 | HA | Light Blue | Light Blue |
| $C^s$ 24 | PKK223-3 | HA | Blue | White |
| $C^s$ 25 | PKK223-3 | HA | Blue | White |
| $C^s$ 26 | PKK223-3 | HA | Blue | White |
| $C^s$ 28 | PKK223-3 | HA | Blue | White |
| $C^s$ 29 | PKK223-3 | HA | Light Blue | Light Green |
| $C^s$ 31 | PKK223-3 | HA | Blue | Light Green |
| $C^s$ 32 | PKK223-3 | HA | Blue | Light Green |

*β-galactosidase activity measured on X-gal plates by the degree of blueness exhibited by colonies; i.e., blue = wild-type activity; white = inactive or no β-galactosidase activity; and green = intermediate activity.

The colonies from all the temperature conditional mutants listed above do turn light to medium blue on X-gal plates after 1–3 weeks at 4° C.

Selection of pH Sensitive Mutants

Similarly, the same mutations may be screened for pH sensitivity as follows: Since the controlled fermentation is normally stopped at pH 5.5 or less, it was felt that mutants which began to exhibit the desirable characteristics (decreased rate of acidification) at about pH 5.5–6.0 would be useful under production and storage conditions of pH of about 4.5 and below.

A nitrocellulose filter is placed on a Luria Agar carbenicillin plate. The transformed *E. coli* are spread on top and colonies grown overnight at 37° C. Two nitrocellulose replica filters are made from this master. The cells are lysed by 3 minute chloroform exposure. The control filter is placed in 25 ml of a 20 nM $MgSO_4$ pH7, 10 mM $NaH_2PO_4$, 50 mM NaOAc buffer for 15 minutes and transferred to the same buffer containing 0.2 ml 2% X-gal. The other filter is placed in a low pH (5–5.5) 100 mM $NaH_2PO_4$, 2 mM $MgSO_4$, 50 mM NaOAc buffer for 15 minutes. Then the filter is transferred to a low pH buffer containing X-gal. A positive colony is one that is blue at pH 7 and white at pH 4.5 or 5.0.

Deletion of the host β-galactosidase (or permease) and reincorporation of the mutant gene back into *L. bulgaricus* can then be done by one skilled in the art. For example, the methods in *Journal of Bacteriology*, May 1984, pp. 411–418 and *Journal of Bacteriology*, November 1988, pp. 5102–5109 would generate the necessary reincorporation mutant *L. bulgaricus* organisms.

RESULTS

Low $pH^s$ β-Galactosidase Mutants

Source: Isolated from methoxyl amine mutagenesis of mutant $C^s4$

First screen: performed at pH 5

| | PHENOTYPE | | | |
|---|---|---|---|---|
| | After 40 minutes | | After 24 hours | |
| MUTANT | pH 5 | pH 7 | 37° C. | 4° C. |
| $pH^s8$-1 | White | White | Blue | Light Green White |
| $pH^s8$-2 | White | Blue | Light Green | Light Blue |
| $pH^s8$-3 | White | Blue | Blue | Light Blue |
| $pH^s8$-4 | White | Blue | Not Tested | |
| $pH^s8$-5 | White | Blue | Blue | Blue |
| $pH^s8$-6 | White | Blue | Blue | Blue |
| $pH^s8$-7 | White | Blue | Blue | Blue |
| $pH^s8$-8 | White | Blue | Light Blue | Light Blue |
| CONTROL PKK223-3 | Light blue | Blue | Blue | Blue |

Second screen: performed at pH 5.5

| | PHENOTYPE | | | |
|---|---|---|---|---|
| | After 30 minutes | | After 24 hours | |
| MUTANT | pH 5.5 | pH 7 | 37° C. | 4° C. |
| $pH^s2$-1 | White | Blue | Light Blue | Light Blue |
| $pH^s2$-2 | White | Blue | Light Blue | Blue + White |
| CONTROL pKK223-2 | Light Blue | Blue | Blue | Blue |

Purification and Characterization of Mutant and Wild-type β-Galactosidase

Mutant and wild-type enzyme could be purified from *E. coli* by the following protocol:

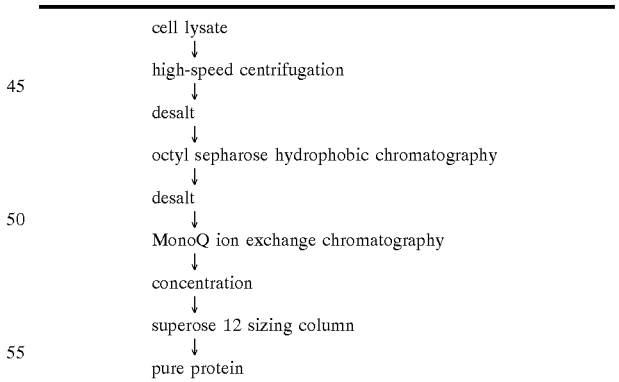

cell lysate
↓
high-speed centrifugation
↓
desalt
↓
octyl sepharose hydrophobic chromatography
↓
desalt
↓
MonoQ ion exchange chromatography
↓
concentration
↓
superose 12 sizing column
↓
pure protein Enzyme purified by this procedure was measured for activity at a variety of temperatures from 10°–40° C. A plot of the log of the apparent initial rate constant vs. the reciprocal of the absolute temperature for two concentrations of mutant $C^s4$ and wild-type enzyme was conducted. While the slope of the wild-type enzyme is linear over the entire temperature range, the mutant clearly shows a decrease in rate below 8° C. Furthermore, above 20° C. the slope for both the wild-type and mutant enzymes are identical. The data clearly indicates that a $C^s4$ enzyme has been produced which is equal in activity to wild-type at production temperatures but reduced in activity at storage temperatures.

We claim:

1. A method of making a fermented food product comprising:
   (a) providing a Lactobacillus comprising an introduced gene encoding a mutant β-galactosidase having a mutation in the amino acid sequence of a native *L. bulgaricus* β-galactosidase wherein said mutant β-galactosidase catalyzes the lysis of β-galactose at a rate at least 20% less than that of said native *L. bulgaricus* β-galactosidase at a temperature of 20° C. or less or a pH of 5.5 or less, but wherein said mutant β-galactosidase catalyzes said lysis at at least 90% of the rate of said native *L. bulgaricus* β-galactosidase under fermentation conditions of the food;
   (b) adding the Lactobacillus of step (a) to an unfermented food product; and
   (c) fermenting the mixture of step (b) under conditions favorable for production of the fermented food product.

2. The method of claim 1, wherein the fermented food product is a dairy product.

3. The method of claim 1, wherein the β-galactosidase produced by said Lactobacillus is only said mutant β-galactosidase.

4. The method of claim 1 wherein said mutant β-galactosidase catalyzes the lysis of β-galactose at a rate at least 20% less than that of said native *L. bulgaricus* β-galactosidase at a temperature of 4°–10° C.

5. A method to prepare yogurt, which method comprises:
   (a) providing *S. thermophilus* and *L. bulgaricus* organisms suitable for making yogurt, the *L. bulgaricus* organisms comprising an introduced a gene encoding a mutant β-galactosidase having a mutation in the amino acid sequence of a native *L. bulgaricus* β-galactosidase whereby said mutant β-galactosidase catalyzes the lysis of β-galactose at a rate of at least 20% less than said native *L. bulgaricus* β-galactosidase at a temperature of 20° C. or less or a pH of 5.5 or less, but wherein said mutant β-galactosidase catalyzes said lysis at at least about 90% of the rate of said native β-galactosidase under the fermentation conditions of yogurt;
   (b) adding the organisms of step (a) to milk;
   (c) fermenting the mixture of step (b) under conditions favorable for the production of yogurt; and
   (d) reducing the temperature of the fermented mixture of (c) to a temperature below 20° C.

6. The method of claim 5, wherein the β-galactosidase produced by said *L. bulgaricus* is only said mutant β-galactosidase.

* * * * *